United States Patent [19]

Horton et al.

[11] Patent Number: 4,537,882
[45] Date of Patent: Aug. 27, 1985

[54] 4-DEMETHOXY-3'-DESAMINO-2'-HALO-ANTHRACYCLINE AND PHARMACEUTICAL COMPOSITION CONTAINING SAME

[75] Inventors: Derek Horton, Columbus; Waldemar Priebe, Plain City, both of Ohio

[73] Assignee: Ohio State University, Columbus, Ohio

[21] Appl. No.: 609,072

[22] Filed: May 10, 1984

[51] Int. Cl.$^3$ .................. A61K 31/70; C07H 15/24
[52] U.S. Cl. .................... 514/34; 260/365; 536/6.4
[58] Field of Search .............. 424/180; 536/6.4; 514/34

[56] References Cited

U.S. PATENT DOCUMENTS

| | | | |
|---|---|---|---|
| 4,046,878 | 9/1977 | Patelli et al. | 424/180 |
| 4,058,519 | 11/1977 | Arcamone et al. | 424/180 |
| 4,166,848 | 9/1979 | Bernardi et al. | 536/6.4 |
| 4,201,773 | 5/1980 | Horton et al. | 424/180 |
| 4,345,070 | 8/1982 | Suarato et al. | 536/6.4 |
| 4,427,664 | 1/1984 | Horton et al. | 424/180 |

Primary Examiner—Johnnie R. Brown
Attorney, Agent, or Firm—Biebel, French & Nauman

[57] ABSTRACT

Compounds of the formula (I), acid addition salts thereof, and pharmaceutical preparations containing the same are disclosed

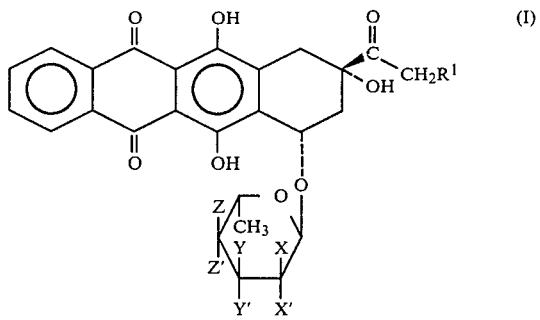

wherein $R^1$ is hydroxy; one of X and X' is hydrogen and the other is a halogen atom selected from the group consisting of fluorine, chlorine, bromine, and iodine; one of Y and Y' is hydrogen and the other is selected from the group consisting of hydrogen, hydroxy and —OCOR; one of Z and Z' is hydrogen and the other is hydrogen, hydroxy or —OCOR; and R is a lower alkyl group.

12 Claims, No Drawings

4-DEMETHOXY-3'-DESAMINO-2'-HALO-ANTHRACYCLINE AND PHARMACEUTICAL COMPOSITION CONTAINING SAME

BACKGROUND OF THE INVENTION

Anthracycline antibiotics including doxorubicin, daunorubicin, and carminomycin have emerged as important chemotherapeutic agents in the treatment of a broad spectrum of neoplastic conditions including acute myloblastic and lymphoblastic leukemias. Doxorubicin (also known as Adriamycin) is the subject of U.S. Pat. No. 3,590,028 and is a prescribed antineoplastic agent used in a number of chemotherapeutic treatments.

The high level of effectiveness and broad spectrum of activity of Adriamycin have lead to numerous efforts to develop anthracycline derivatives which exhibit less toxicity and enhanced activity. Among the derivatives that have been developed and investigated are 4-demethoxyadriamycin, 4-demethoxydaunomycin and certain halogenated derivatives in which the 1- or 2-position in the sugar moiety is substituted by a halogen atom.

2'-Halo derivates of daunomycin, demethoxydaunomycin, doxorubicin and carminomycin are disclosed in U.S. Pat. No. 4,427,664 to Horton et al. U.S. Pat. No. 4,058,519 to Arcamone et al teaches adriamycin derivatives and reactive intermediates, for example, 1-halo-2,3,6-tridoexy-3-fluoroacetamido-4-trifluoroacetoxy-α-L-lyxo or arabino)hexopyranoses. U.S. Pat. No. 4,046,878 to Patelli et al indicates that the reaction proceeds from daunomycin analogs and uses as a sugar the 1-chloro-2,3,6-trideoxy-3-trifluoroacetamido-4-trifluoroacetoxy-α-L-lyxo pyranose.

SUMMARY OF THE INVENTION

The present invention relates to a novel anthracycline antiobiotic which is represented by the formula (I):

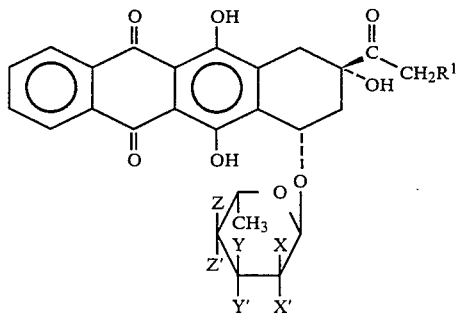

wherein R' is hydroxy; one of X and X' is hydrogen and the other is a halogen atom selected from the group consisting of fluorine, chlorine, bromine, and iodine; one of Y and Y' is hydrogen and the other is selected from the group consisting of hydrogen, hydroxy and —OCOR; one of Z and Z' is hydrogen and the other is hydrogen, hydroxy or —OCOR wherein R is a lower alkyl group preferably having 1 to 4 carbon atoms.

The present invention also provides pharmaceutical preparations containing the novel compounds of the present invention as active agents. These compositions can be prepared by dispersing or dissolving the compounds or their acid addition salts in any pharmaceutically acceptable non-toxic carrier suitable for the desired mode of administration. Therapeutic compositions of the present invention may be administered parentally by intravenous, intramuscular, intraperitoneal, or other conventional injection. Preferably, the carrier is an aqueous medium buffered to pH 7.2–7.5, the physiological range. Any suitable conventional buffer can be used such as tris phosphates, bicarbonates or citrates. If desired, saline solution can be used.

In a more particular embodiment, the present invention provides compounds of the formula (I) wherein X' is bromine or iodine; and one of Y and Y' and one of Z and Z' is acetoxy or hydroxy.

In a still more particular embodiment, the present invention provides compounds of the formula (I) wherein X' is iodine and Z' is acetoxy or hydroxy.

The compounds of the present invention exhibit a broad spectrum of anti-cancer activity and are effective in the treatment of myelobastic and lymphoblastic leukemia, and melanoma. The compounds can be administered by intravenous or intraperitoneal injection in an aqueous medium buffered to the physiological range.

DETAILED DESCRIPTION OF THE INVENTION

The compounds of the present invention are derivatives of 4-demethoxydoxorubicin. These compounds are coupled at the 0–7 position of the aglycon with a 2-substituted halo pyranose or furanose ring structure of sugars which are pentose or hexose varieties. Of the halogens, iodine is preferred but bromine, chlorine and fluorine may also be useful. Preferred are α-L-manno or α-L-talo hexopyranose, which sugar isomers particularly sustain or potentiate the biological activity of the coupled compound.

A synthesis suitable for preparing the compounds of the present invention is diagrammed below:

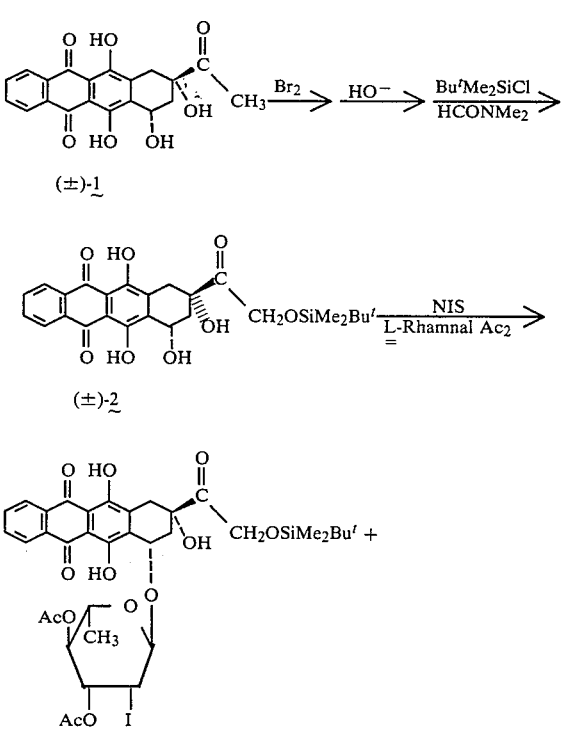

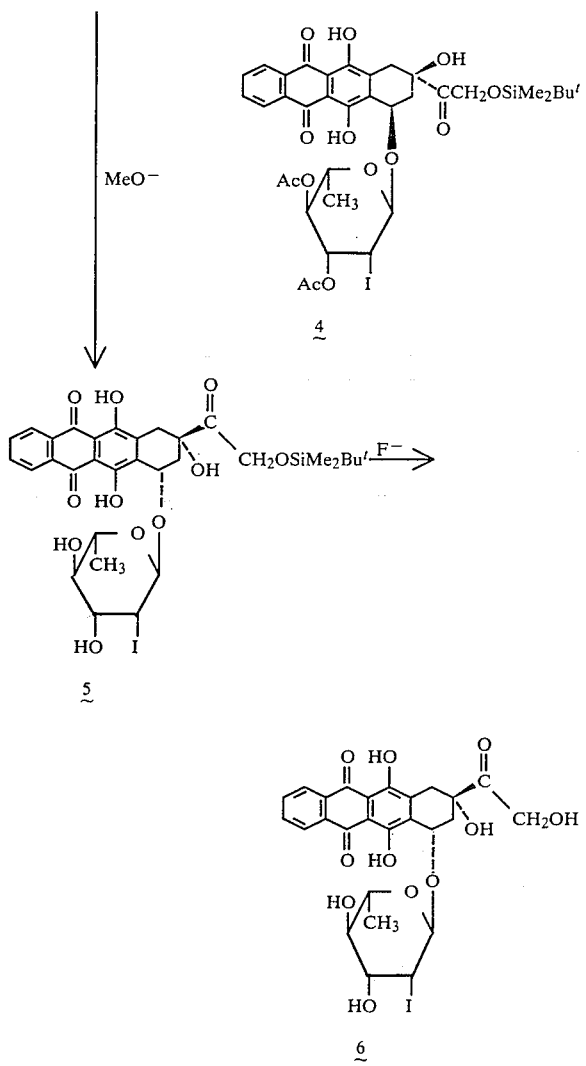

Racemic 4-demethoxydaunomycinone (1) is converted into its 14-bromo derivative by dissolving (1) in chloroform and adding with stirring bromine in chloroform. The general procedure is described by Smith et al, *J. Org. Chem.*, 42 (1977) 3653–3660. The bromo derivative is then readily hydrolyzed by 5% aqueous potassium carbonate in 0.5 hr at 25° C. to afford racemic 4-demethoxyadriamycinone. Alternatively, the bromo derivative may be hydrolyzed by heating to 80° C. in dimethyl sulfoxide water solution for 0.5 to 1 hr. The latter is silylated with tert-butylchlorodimethyl-silane in N,N-dimethylformamide (DMF) in the presence of imidazole to give racemic 14-O-tert-butyldimethylsilyl-4-demethoxyadriamycinone (2). The reaction of L-rhamnal diacetate and N-iodosuccinimide (NIS) with (2) gives a chromatographically separable mixture of (7S,9S)-14-O-tert-butyldimethylsilyl-4-demethoxy-7-O-(3,4-di-O-acetyl-2,6-dideoxy-2-iodo-α-L-manno-hexopyranosyl)adriamycinone (3) and its (7R,9R) isomer (4). O-Deacetylation of (3) by conventional saponification with sodium methoxide to give (5), followed by fluoride ion-mediated deprotection at 0–14, furnishes the optically pure, antitumor-active product, (7S,9S)-4-demethoxy-7-O-(2,6-dideoxy-2-iodo-α-L-manno-hexopyranosyl)-adriamycinone (6).

The synthesis of the compounds of the present invention is illustrated in more detail by the following non-limiting examples:

SYNTHESIS EXAMPLE 1

Racemic 14-O-tert-butyldimethylsilyl-4-demethoxyadriamycinone (2)

Racemic 4-demethoxyadriamycinone (891.2 mg, 2.32 mmol), obtained by the process of Smith et al, was dissolved in DMF (12 ml) and imidazole (686 mg, 10.1 mmol) and tert-butylchlorodimethylsilane (559.4 mg, 3.71 mmol) was added. The mixture was stirred for 0.5 hr. at 25° and then poured into dichloromethane. The solution was then washed with water. The organic extract was dried with sodium sulfate and evaporated to give a dark-red oil that was chromatographed on silica gel (100 g) with 20:1 toluene-acetone as eluant. Evaporation of the main fraction gave compound (2), yield 629 mg (54%); m.p. 193°–195°; $^1$H-n.m.r. (200 MHz, CDCl$_3$): 13.60, 13.28 (s, 1H, HO-6,11), 8.35, 7.84 (m, 2H, H-1,2,3,4), 5.34 (m, 1H, H-7) 4.86 (AB m, 2H, H-14A,14B), 4.54 (s, 1H, HO-9), 3.54 (bd, 1H, HO-7), 3.26 (dd, 1H $J_{8e,10e}$ 1.8 Hz, H-10e), 3.03 (d, 1H, $J_{10a,10e}$ 18.6 Hz, H-10a), 2.39 (bd, 1H, H-8e), 2.22 (dd, 1H, $J_{7,8a}$ 4.5, $J_{8a,8e}$ 14.8 Hz, H-8a), 0.95 (s, 9H, CMe$_3$), 0.15 (s, 6H, SiMe$_2$).

Anal. Calc. for C$_{26}$H$_{30}$O$_8$Si: C, 62.63; H, 6.06. Found: C, 62.37; H, 6.08.

SYNTHESIS EXAMPLE 2

(7S,9S)-14-O-(tert-Butyldimethylsilyl)-4-demethoxy-7-O-(3,4-di-O-acetyl-2,6-dideoxy-2-iodo-α-L-manno-hexopyranosyl)adriamycinone (3) and (7R,9R)-14-O-(tert-butyldimethylsilyl)-4-demethoxy-7-O-(3,4-di-O-acetyl-2,6-dideoxy-2-iodo-α-L-manno-hexo-pyranosyl)adriamycinone (4)

i. Compound (2) (629 mg, 1.26 mmol) was dissolved in oxolane (8 ml) and then 3,4-di-O-acetyl-L-rhamnal (417 mg, 1.95 mmol) in acetonitrile (15 ml) was added. The solution was maintained under an atmosphere of dry argon and N-iodosuccinimide (604 mg, 2.68 mmol) was added with stirring. After 3 hrs, further portions of 3,4-di-O-acetyl-L-rhamnal (410 mg, 1.91 mmol) and N-iodosuccinimide (594 mg, 2.64 mmol) were added. The reaction was terminated after a further 3 hrs by pouring the mixture into dichloromethane (150 ml) and sequentially washing the solution with 10% aqueous sodium thiosulfate and water. The organic phase was dried with magnesium sulfate and evaporated.

ii. Column chromatography of the product-mixture on silica gel (100 g) with 50:1 toluene-acetone as eluant and crystallization afforded compound (4) (7R,9R) as the less-polar component; yield 141 mg (27%); m.p. 153°, $^1$H-n.m.r. (200 MHz, CDCl$_3$): 13.69, 13.30 (s, 1H, HO-6,11), 8.36, 7.86 (m, 2H, H-1,2,3,4), 5.53 (d, 1H, H-1'), 5.50 (m, 1H, H-7), 5.15 (t, 1H, H-4'), 4.93 (d, 1H, H-14A), 4.84 (d, 1H, H-14B), 4.53 (dd, 1H, $J_{1',2'}$ 1.6, $J_{2',3'}$ 4.3 Hz, H-2'), 4.44 (dd, 1H, $J_{3',4'}$ 8.9 Hz, H-3'), 4.26 (qd, 1H, $J_{4',5'}$ 10.2, $J_{5',6'}$ 6.2 Hz, H-5'), 4.19 (s, 1H, HO-9), 3.31 (bd, 1H, H-10e), 3.15 (d, 1H, $J_{10a,10e}$ 19.4 Hz, H-10a), 2.43 (bd, 1H, $J_{8a,8e}$ 14.9 Hz, H-8e), 2.06, 2.04 (s, 7H, 2×OAc, H-8a), 1.25 (d, 3H, H-6'), 0.96 (s, 9H, CMe$_3$), 0.15, 0.14 (s, 3H, Me$_2$Si).

Anal. Calc. for $C_{36}H_{43}IO_{13}Si$: C, 51.55; H, 5.17; I, 15.13. Found: C, 51.39; H, 5.17; I, 15.23.

The more polar diastereomer (3), having the 7S,9S configuration, was isolated in a yield of 155.2 mg (29%). Recrystallization from acetone-hexane gave a red solid having m.p. 128°–130°, $[\alpha]_D{}^{22} +44°$ (c 0.03, chloroform); $^1$H-n.m.r. (200 MHz, CDCl$_3$): 13.59, 13.31 (s, 1H, HO-6,11), 8.37, 7.85 (m, 2H, H-1,2,3,4), 5.75 (s, 1H, H-1'), 5.26 (dd, 1H, H-7), 5.19 (t, 1H, $J_{4',5'}$ 9.8 Hz, H-4'), 4.63 (dd, 1H, $J_{1',2'}$ 1.4 Hz, H-2'), 4.36 (dd, 1H, $J_{2',3'}$ 4.4, $J_{3',4'}$ 9.3 Hz, H-3'), 4.10 (qd, 1H, H-5'), 4.08 (s, 1H, HO-9), 3.31 (dd, 1H, $J_{8e,10e}$ 1.0 Hz, H-10e), 3.07 (d, 1H, $J_{10a,10e}$ 18.9 Hz, H-10a), 2.36 (bd, 1H, H-8e), 2.22 (dd, 1H, $J_{7,8a}$ 4.2, $J_{8a,8e}$ 15.5 Hz, H-8a), 2.07, 2.05 (s, 3H, OAc), 1.29 (d, 3H, $J_{5',6'}$ 6.3 Hz, H-6'), 0.96 (s, 9H, CMe$_3$), and 0.15 (s, 6H, Me$_2$Si).

Anal. Calc. for $C_{36}H_{43}IO_{13}Si$: C, 51.55; H, 5.17; I, 15.13. Found: C, 51.44; H, 5.18; I, 15.02.

SYNTHESIS EXAMPLE 3

(7S,9S)-14-O-(tert-butyldimethylsilyl)-4-demethoxy-7-O-(2,6-dideoxy-2-iodo-α-L-manno-hexopyranosyl)adriamycinone (5)

Compound (3) (197 mg, 0.23 mmol) was dissolved in methanol (12 ml) and then methanolic sodium methoxide (1.7 ml of 0.45 mmol/ml) was added. The reaction was subsequently terminated by making the solution neutral with solid carbon dioxide, whereupon thin layer chromatography (4:1 toluene-acetone) showed (3) to be absent. The solution was poured into water and the product extracted with dichloromethane. The organic phase was washed twice with water, dried with magnesium sulfate, and evaporated under diminished pressure. Crystallization from acetone-hexane gave 90.5 mg (51%) of compound (5) as red crystals having m.p. 179°–181°, $[\alpha]_D{}^{22} +15°$ (c 0.03, chloroform); $^1$H-n.m.r. (200 MHz, CDCl$_3$): 13.61, 13.28 (s, 1H, HO-6,11), 8.35, 7.85 (m, 2H, H-1,2,3,4), 5.77 (s, 1H, H-1'), 5.24 (dd, 1H, $J_{7,8e}$ 1.9 Hz, H-7), 4.88 (AB pattern, 2H, H-14), 4.54 (dd, 1H, $J_{1',2'}$ 1.0 Hz, H-2'), 4.12 (s, 1H, HO-9), 3.94 (dq, 1H, $J_{4',5'}$ 9.3, $J_{5',6'}$ 6.3 Hz, H-5'), 3.58 (td, 1H, $J_{3',4'}$ 9.1, $J_{4',HO-4'}$ 3.2 Hz, H-4'), 3.27 (dd, 1H, $J_{8e,10e}$ 1.3 Hz, H-10e), 3.04 (d, 1H, $J_{10a,10e}$ 19.0 Hz, H-10a), 2.85 (ddd, 1H, $J_{2',3'}$ 4.1, $J_{3',HO-3'}$ 7.6 Hz, H-3'), 2.38 (bd, 1H, $J_{8a,8e}$ 15.0 Hz, H-8e), 2.32 (d, 1H, HO-4'), 2.21 (dd, 1H, $J_{7,8a}$ 4.2 Hz, H-8a), 1.39 (d, 3H, H-6') 0.95 (s, 9H, CMe$_3$), 0.14 (s, 6H, Me$_2$Si); signals of HO-3',4',6,9 and -11 disappeared when a drop of D$_2$O was added; $^{13}$C-n.m.r. (50 MHz, CDCl$_3$): 210.8 (C=O), 186.8, 186.6 (C-5,12), 156.4, 156.2 (C-6,11), 135.7, 134.7, 133.4, 133.3, 132.6, 127.2, 127.0 (C-1,2,3,4,4a,6a,10a,12a), 111.7, 111.0 (C-5a,11a) 104.8 (C-1'), 76.9 (C-9), 75.5 (C-4'), 70.5 (C-5',7), 69.3 (C-3'), 66.6 (C-14), 36.9 (C-2'), 35.6 (C-8), 34.0 (C-10), 25.9 (C$\underline{\text{Me}}_3$), 18.5 ($\underline{\text{C}}$Me$_3$), 17.6 (C-6'), −5.3, −5.4 (Me$_2$Si).

Anal. Calc. for $C_{32}H_{39}IO_{11}Si$: C, 50.93; H, 5.21; I, 16.82. Found: C, 50.76; H, 5.26; I, 16.91.

SYNTHESIS EXAMPLE 4

(7S,9S)-4-Demethoxy-7-O-(2,6-dideoxy-2-iodo-α-L-manno-hexopyranosyl)adriamycinone (6)

Compound (5) (90.0 mg, 0.12 mmol) was dissolved in a mixture of dichloromethane (1 ml) and oxolane (5 ml), and then pyridine (50 μl) and 180 μl of a 1M solution of tetrabutylammonium fluoride in oxolane was added. The reaction was terminated after 40 min by dilution with dichloromethane and washing with water. The organic phase was dried with magnesium sulfate and evaporated under diminished pressure. Crystallization from dichloromethane-acetone-hexane gave 31 mg (41%) of a red solid, m.p. 173°–175° (dec.); $^1$H-n.m.r. (200 MHz, acetone-d$_6$): 8.38, 8.01 (m, 2H, H-1,2,3,4), 5.73 (s, 1H, H-1'), 5.26 (dd, 1H, $J_{7,8a}$ 5.0, $J_{7,8e}$ 3.0 Hz, H-7), 4.52 (dd, $J_{1',2'}$ 1.0, $J_{2',3'}$ 4.0 Hz, H-2').

As demonstrated by the following biological examples, the compounds of the present invention display significant anticancer activity in animals with less toxicity than 4-demethoxydoxorubicin. Among other effects, the compounds of the present invention show antileukemic activity against murine P388 leukemia and B-16 melanoma. Furthermore, when administered in their optimum dosage, the compounds of the present invention are accompanied by less incidence of lesions.

BIOLOGICAL EXAMPLE 1

Groups of mice were inoculated by intraperitoneal injection with the lymphocytic leukemia cell line P-388 or the solid tumor cell line B-16 melanoma. On day 1, 24 hours after implantation of the tumor cells, groups of test mice were administered a single intraperitoneal dose of the compound 4-demethoxy-7-O-(2-iodo-2,6-dideoxy-α-L-manno-hexapyranosyl)adriamycinone.

For comparative purposes, similar groups of mice challenged with the P-388 or B-16 tumor cells were given a single dose of doxorubicin hydrochloride on day 1 following implantation of the tumor cells. The animals were observed and their survival compared with that of control animals which received the same tumor inoculation but were not treated with the drug. The T/C, a ratio of the test Median Survival Time (MST) relative to control MST was determined. An increase in the T/C indicates an increase in the antitumor activity of the compound. If T/C is less than 100, the compound is considered toxic. Testing in the P-388 line showed that compound 6 administered at a dosage of 3.12 mg/kg demonstrated a T/C of 218. A doxorubicin hydrochloride dosage of 5 mg/kg showed a T/C of 180. Compound 6 also demonstrated activity in the more resistant B-16 solid tumor. Dosages of 5 and 2.5 mg/kg were active with T/C of 184 and 177 respectively. A 20 mg/kg doxorubicin hydrochloride dosage elicited a T/C of 104.

BIOLOGICAL EXAMPLE 2

Additional studies were performed to examine the extravasation potential of 4-demethoxy-7-O-(2-iodo-2,6-dideoxy-α-L-manno-hexapyranosyl)adriamycinone.

Groups of mice (10/group) were injected subcutaneously with 0.2 ml or 0.1 ml of the test compound suspended in cremophor at a concentration of 1.0 mg/ml. Similar groups were given 0.2 ml or 0.1 ml of doxorubicin hydrochloride suspended in cremophor at a concentration of 2.0 mg/ml. Control groups received 0.2 ml of cremophor. The animals were observed frequently for lesions. The test showed that the number of animals with demonstrable lesions in the groups administered the test compound were substantially lower in comparison to those noted in groups administered doxorubicin hydrochloride. The results are reported in the Table below.

TABLE

|  | Dosage | Number of animals with lesions | |
|---|---|---|---|
|  |  | Day 5 | Day 9 |
| Compound 6 | 0.1 mg | 1/10 | 1/10 |

TABLE-continued

| | Dosage | Number of animals with lesions | |
| --- | --- | --- | --- |
| | | Day 5 | Day 9 |
| Doxorubicin | 0.2 mg | 6/10 | 10/10 |
| Compound 6 | 0.2 mg | 1/10 | 3/10 |
| Doxorubicin | 0.4 mg | 8/10 | 10/10 |
| Cremophor (control) | 0.2 mg | 0/10 | 0/10 |

Having described the invention in detail and by reference to specific embodiments thereof, it will be apparent that numerous variations are possible without departing from the spirit and scope of the invention defined by the following claims.

What is claimed is:

1. Compounds of the formula (I)

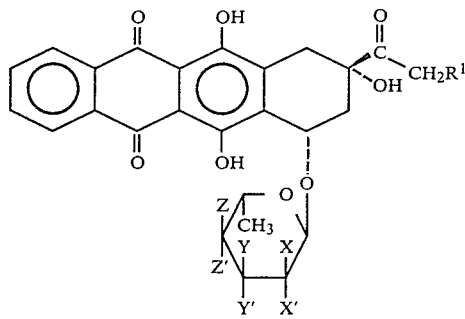

wherein $R^1$ is hydroxy; one of X and X' is hydrogen and the other is a halogen atom selected from the group consisting of fluorine, chlorine, bromine, and iodine; one of Y and Y' is hydrogen and the other is selected from the group consisting of hydrogen, hydroxy and —OCOR; one of Z and Z' is hydrogen and the other is hydrogen, hydroxy or —OCOR, and R is a lower alkyl group.

2. The compounds of claim 1 wherein X' is iodine or bromine.

3. The compounds of claim 1 wherein X' is iodine.

4. The compounds of claim 2 wherein Z or Z' is hydroxy or —OCOR where R is a lower alkyl group.

5. The compounds of claim 3 wherein Z or Z' is hydroxy or —OCOR where R is a lower alkyl group.

6. The compounds of claim 1 wherein said compound is 4-demethoxy-7-O-(2-iodo-2,6-dideoxy-α-L-manno-hexopyranosyl)adriamycinone.

7. A pharmaceutical preparation useful for treating the growth of implanted tumors comprising a carrier and a therapeutically effective amount of a compound of the formula

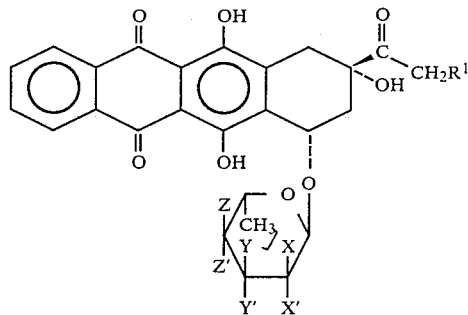

wherein $R^1$ is hydroxy; one of X and X' is hydrogen and the other is a halogen atom selected from the group consisting of fluorine, chlorine, bromine, and iodine; one of Y and Y' is hydrogen and the other is selected from the group consisting of hydrogen, hydroxy and —OCOR; one of Z and Z' is hydrogen and the other is hydrogen, hydroxy or —OCOR, and R is a lower alkyl group; or a pharmaceutically acceptable acid addition salt thereof.

8. The pharmaceutical preparation of claim 7 wherein X' is iodine or bromine.

9. The pharmaceutical preparation of claim 7 wherein X' is iodine.

10. The pharmaceutical preparation of claim 8 wherein Z or Z' is —OCOR or hydroxy where R is a lower alkyl group.

11. The pharmaceutical preparation of claim 9 wherein Z or Z' is —OCOR or hydroxy where R is a lower alkyl group.

12. The pharmaceutical preparation of claim 7 wherein said compound is 4-demethoxy-7-O-(2-iodo-2,6-dideoxy-α-L-manno-hexopyranosyl)adriamycinone.

* * * * *